(12) United States Patent
Hampel et al.

(10) Patent No.: US 6,298,117 B1
(45) Date of Patent: Oct. 2, 2001

(54) VARIABLE APERTURE Z-AXIS TRACKING COLLIMATOR FOR A COMPUTED TOMOGRAPH SYSTEM

(75) Inventors: Willi W. Hampel, St. Francis; Russell W. Hum, Waukesha; Carmine F. Vara, Jr., New Berlin; Steven J. Woloschek, Franklin, all of WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/693,367

(22) Filed: Oct. 20, 2000

Related U.S. Application Data (63) Continuation of application No. 09/140,108, filed on Aug. 25, 1998, now Pat. No. 6,173,039.

(51) Int. Cl.$^7$ ....................................................... A61B 6/03
(52) U.S. Cl. ........................... 378/150; 378/147; 378/156; 378/157
(58) Field of Search .................................. 378/4, 65, 147, 378/150, 151, 156, 157, 158, 901

(56) References Cited

U.S. PATENT DOCUMENTS

| | | | |
|---|---|---|---|
| 4,361,902 | * | 11/1982 | Brandt et al. .......................... 378/150 |
| 4,868,843 | * | 9/1989 | Nunan .................................. 378/157 |
| 4,991,189 | | 2/1991 | Boomgaarden et al. . |
| 5,090,037 | | 2/1992 | Toth et al. . |
| 5,430,784 | | 7/1995 | Ribner et al. . |
| 5,644,614 | * | 7/1997 | Toth et al. ............................. 378/147 |
| 5,867,555 | | 2/1999 | Popescu et al. . |
| 5,949,811 | * | 9/1999 | Baba et al. .............................. 378/97 |
| 5,982,846 | * | 11/1999 | Toth et al. ............................ 378/901 |
| 6,056,437 | * | 5/2000 | Toth ..................................... 378/205 |
| 6,061,419 | * | 5/2000 | Hsieh et al. .............................. 378/4 |
| 6,173,039 | * | 1/2001 | Hample et al. ....................... 378/150 |

* cited by examiner

*Primary Examiner*—Drew Dunn
(74) *Attorney, Agent, or Firm*—Armstrong Teasdale LLP; Christian G. Cabou (57) ABSTRACT

Methods and apparatus for dose reduction in a computed tomography (CT) system are described. In one embodiment, the CT system includes a pre-patient collimator and a configurable multislice detector array. The pre-patient collimator includes a plurality of eccentric cams and a filtration device for altering the x-ray beam radiated from a x-ray source. The eccentric cams are positioned to collimate the x-ray beam and may be independently positioned to provide z-axis correction of the x-ray beam. The filtration device includes a plurality of filters for altering the x-ray beam. In operation, an operator selects the type of test and the quantity and thickness of the slices. After altering the detector and collimator configuration, slice data for each slice is gathered.

24 Claims, 5 Drawing Sheets

VARIABLE APERTURE Z-AXIS TRACKING COLLIMATOR FOR A COMPUTED TOMOGRAPH SYSTEM

This application is a continuation of Ser. No. 09/140,106 Aug. 25, 1998, U.S. Pat. No. 6,173,039.

BACKGROUND OF THE INVENTION

This invention relates generally to computed tomograph (CT) imaging and, more particularly, to reducing x-ray exposure and improving x-ray efficiency in a multislice CT system.

In at least some computed tomograph (CT) imaging system configurations, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. X-ray sources typically include x-ray tubes, which emit the x-ray beam at a focal spot. X-ray detectors typically include a post patient collimator for collimating scattered x-ray beams received at the detector. A scintillator is located adjacent the post patient collimator, and photodiodes are positioned adjacent the scintillator.

Multislice CT systems are used to obtain data for an increased number of slices during a scan. Known multislice systems typically include detectors generally known as 3-D detectors. With such 3-D detectors, a plurality of detector elements form separate channels arranged in columns and rows. Each row of detectors forms a separate slice. For example, a two slice detector has two rows of detector elements, and a four slice detector has four rows of detector elements. During a multislice scan, multiple rows of detector cells are simultaneously impinged by the x-ray beam, and therefore data for several slices is obtained.

In known CT systems, the x-ray beam from the x-ray source is projected through a pre-patient collimating device, or collimator, that defines the x-ray beam profile in the patient axis, or z-axis. The collimator includes x-ray absorbing material with an aperture therein for restricting the x-ray beam. The process of restricting the x-ray beam to the desired fan beam profile is termed "collimation".

With respect to restricting the x-ray beam, known collimators typically include two opposing metallic blades that may be opened and closed to change the aperture width. The fan beam "thickness", as measured along the z-axis, can be selected by adjusting the blade orientation. The blades also may be moved in a same direction to displace the centerline of the aperture. Changing the aperture centerline changes the fan beam angle with respect to the z-axis.

In multislice CT systems, it is desirable to have only the umbra of the x-ray beam fall on the detector cells. Although the x-ray beam can initially be collimated so that the penumbra does not fall on the detector cells, thermal expansion of the x-ray source causes z-axis movement of the x-ray source focal spot, causing the x-ray beam not to be centered on the detector. Slice thickness may also be affected by misalignment of the focal spot in the y-dimension, target angle, and the size of the focal spot. Additionally, mechanical forces due to centripetal loading increases as the gantry is rotated, which result in focal spot and fan beam movement. As the fan beam moves, it is possible that at least part of the penumbra will fall on the detector cells. Movement of the fan beam changes the strength of signals from the detector array cells. Such fan beam movement may cause differential gain errors and result in severe ring, band and center artifacts.

Accordingly, it would be desirable to provide a CT system that enables selection of the number and thickness of slices and improve x-ray beam stability and efficiency to reduce patient dosage.

BRIEF SUMMARY OF THE INVENTION

These and other objects may be attained by a CT system which, in one embodiment, utilizes a pre-patient collimator and a configurable multislice detector array to improve x-ray beam stability and efficiency to reduce patient x-ray dosage. The CT system pre-patient collimator includes a plurality of eccentric cams and a filtration device for altering the x-ray beam. The eccentric cams are positioned to collimate the x-ray beam to a selected slice thickness and may be independently positioned to provide z-axis motion correction of the x-ray beam. In one embodiment, the filtration device includes a plurality filters that alter the x-ray beam as the filtration device is moved relative to a collimator housing utilizing a filter motor. The CT system multislice detector, in one embodiment, includes a plurality of detector modules. Each detector module has a photodiode cell array optically coupled to a scintillator array. The photodiode array includes a plurality of photodiodes arranged in rows and columns. Each detector module further includes a switch apparatus and a decoder. The switch apparatus is electrically coupled between the photodiode output lines and a CT system data acquisition system (DAS). The switch apparatus, in one embodiment, is an array of FETs and alters the number of slices and the thickness of each slice by allowing each photodiode output line to be enabled, disabled, or combined with other photodiode output lines.

In operation, an operator determines the type of test to be performed and the quantity and thickness of each slice. The appropriate photodiode outputs of the detector array are then electrically combined to form the selected number of inner slices with each having the selected thickness. The pre-patient collimator cams are then adjusted for the selected thickness and the filters are positioned for the selected test. Slice data for each slice is then gathered from the detector array. If during gathering of the data, the focal spot of the x-ray source moves, the pre-patient collimator cams may be repositioned to properly position the focal spot.

By using the above described CT system the number and thickness of scan slices is selectable. In addition, such CT system improves x-ray beam stability and efficiency and reduces patient x-ray dosage.

DETAILED DESCRIPTION OF THE INVENTION

Set forth below is a description of an exemplary multislice CT system in accordance with one embodiment of the present invention. Although one embodiment of the system is described in detail below, it should be understood that many alternative embodiments of the inventions are possible. For example, although one particular detector and one particular pre-patient collimator are described, other detectors or collimators could be used in connection with the system, and the present invention is not limited to practice with any one particular type of detector. Specifically, the detector described below includes a plurality of modules and each module includes a plurality of detector cells. Rather than the specific detector described below, a detector which has non-segmented cells along the z-axis, and/or a detector which has multiple modules with multiple elements along the x-axis and/or z-axis joined together in either direction to acquire multislice scan data simultaneously, can be utilized. Generally, the system is operable in a multislice mode to collect 1 or more slices of data. Axial and helical scans can be performed with the system, and cross section images of a scanned object can be processed, reconstructed, displayed and/or archived.

Figure 1:
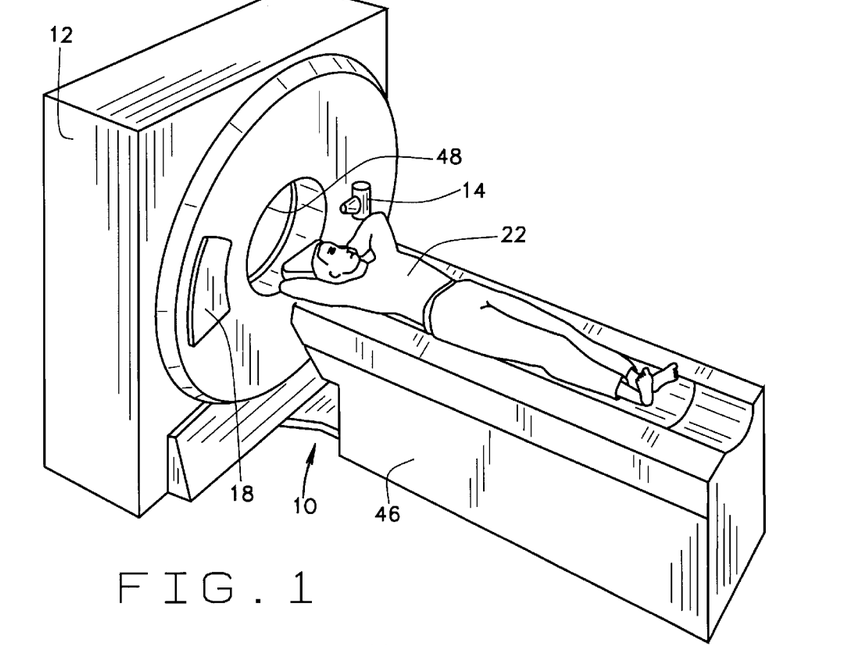
FIG. 1 is a pictorial view of a CT imaging system.
Figure 2:
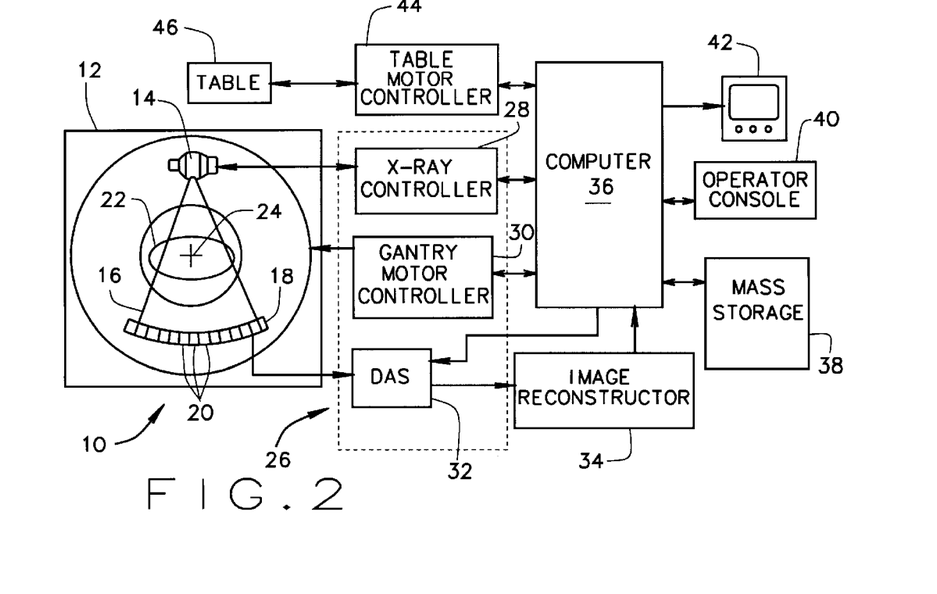
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector modules 20 which together sense the projected x-rays that pass through a medical patient 22. Each detector module 20 produces electrical signals that represent the intensity of impinging x-ray beams and hence the attenuation of the beams as they pass through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector modules 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 also operates a table motor controller 44 which controls a motorized table 46 to position patient 22 in gantry 12. Particularly, table 46 moves portions of patient 22 through a gantry opening 48.

Figure 3:
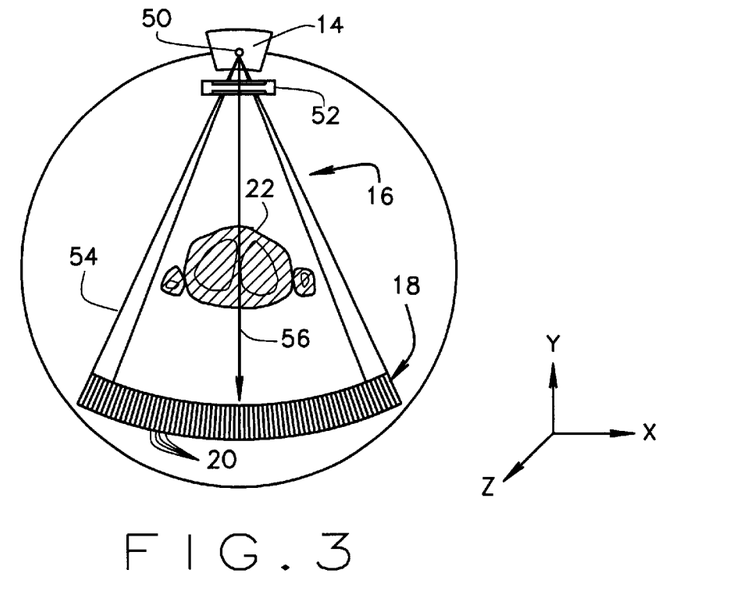
FIG. 3 is a schematic view of the CT imaging system with a collimator.

Referring to FIG. 3, and with respect to operation of x-ray source 14, x-ray beam 16 emanates from a focal spot 50 of source 14. X-ray beam 16 is collimated by pre-patient collimator 52, and a collimated beam 54 is projected toward detector array 18 along a fan beam axis 56 centered within beam 16.

The architecture of system 10 described above provides many important advantages, including that detector array 18 and collimator 52 can be configured so that system 10 reduces x-ray dosage to patient 22 and improves x-ray beam stability and efficiency. Particularly, by configuring detector array 18 and adjusting collimator 52, CT system 10 has a selectable number of slices with each slice having a selectable slice thickness. Further details regarding detector array 18 and collimator 52 are set forth below.

Figures 4, 5:
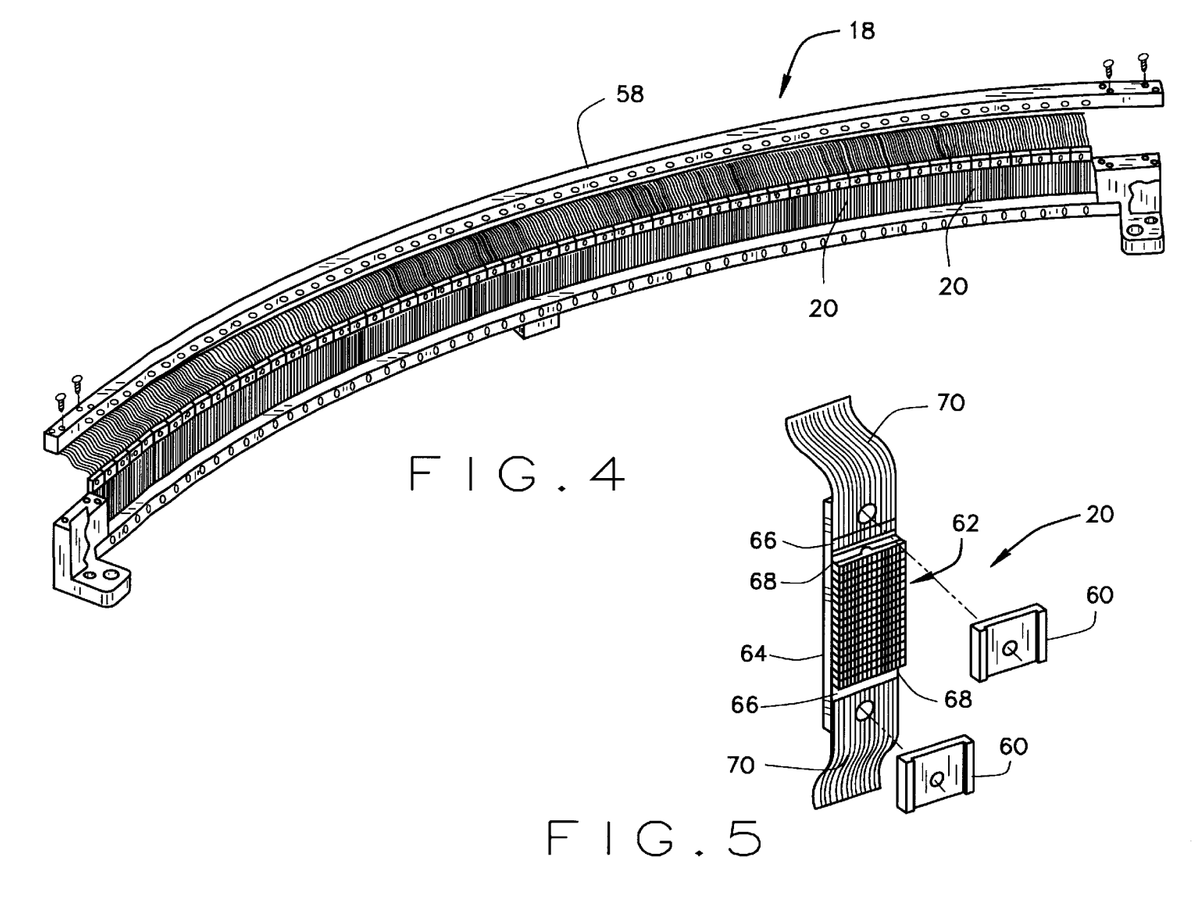
FIG. 4 is a perspective view of a CT system detector array.
FIG. 5 is a perspective view of a detector module.

As shown in FIGS. 4 and 5, detector array 18 includes a plurality of detector modules 20. Each detector module 20 is secured to a detector housing 58 by plates 60. Each module 20 includes a multidimensional scintillator array 62 and a high density semiconductor array (not visible). A post patient collimator (not shown) is positioned over and adjacent scintillator array 62 to collimate x-ray beams before such beams impinge upon scintillator array 62. Scintillator array 62 includes a plurality of scintillation elements arranged in an array, and the semiconductor array includes a plurality of photodiodes (not visible) arranged in an identical array. The photodiodes are deposited, or formed on a substrate 64, and scintillator array 62 is positioned over and secured to substrate 64.

Detector module 20 also includes a switch apparatus 66 electrically coupled to a decoder 68. Switch apparatus 66 is a multidimensional semiconductor switch array of similar size as the photodiode array. In one embodiment, switch apparatus 66 includes an array of field effect transistors (not shown) with each field effect transistor (FET) having an input, an output, and a control line (not shown). Switch apparatus 66 is coupled between the photodiode array and DAS 32. Particularly, each switch apparatus FET input is electrically connected to a photodiode array output and each switch apparatus FET output is electrically connected to DAS 32, for example, using flexible electrical cable 70.

Decoder 68 controls the operation of switch apparatus 66 to enable, disable, or combine the outputs of the photodiode array in accordance with a desired number of slices and slice resolutions for each slice. Decoder 68, in one embodiment, is a decoder chip or a FET controller as known in the art. Decoder 68 includes a plurality of output and control lines coupled to switch apparatus 66 and computer 36. Particularly, the decoder outputs are electrically connected to the switch apparatus control lines to enable switch apparatus 66 to transmit the proper data from the switch apparatus inputs to the switch apparatus outputs. The decoder control lines are electrically connected to the switch apparatus control lines and determine which of the decoder outputs will be enabled. Utilizing decoder 68, specific FETs within switch apparatus 66 are enabled, disable, or combined so that specific outputs of the photodiode array are electrically connected to CT system DAS 32. In one embodiment defined as a 16 slice mode, decoder 68 enables switch apparatus 66 so that all rows of photodiode array 52 are electrically connected to DAS 32, resulting in 16 separate, simultaneous slices of data being sent to DAS 32. Of course, many other slice combinations are possible.

In one specific embodiment, detector 18 includes fifty-seven detector modules 20. The semiconductor array and scintillator array 62 each have an array size of 16×16. As a result, detector 18 has 16 rows and 912 columns (16×57 modules), which enables 16 simultaneous slices of data to be collected with each rotation of gantry 12. Of course, the present invention is not limited to any specific array size, and it is contemplated that the array can be larger or smaller depending upon the specific operator needs. Also, detector 18 may be operated in many different slice thickness and number modes, e.g., one, two, and four slice modes. For example, the FETs can be configured in the four slice mode, so that data is collected for four slices from one or more rows of the photodiode array. Depending upon the specific configuration of the FETs as defined by decoder control lines, various combinations of outputs of the photodiode array can be enabled, disabled, or combined so that the slice thickness may, for example, be 1.25 mm, 2.5 mm, 3.75 mm, or 5 mm. Additional examples include a single slice mode including one slice with slices ranging from 1.25 mm thick to 20 mm thick, and a two slice mode including two slices with slices ranging from 1.25 mm thick to 10 mm thick. Additional modes beyond those described are possible.

Figure 6:
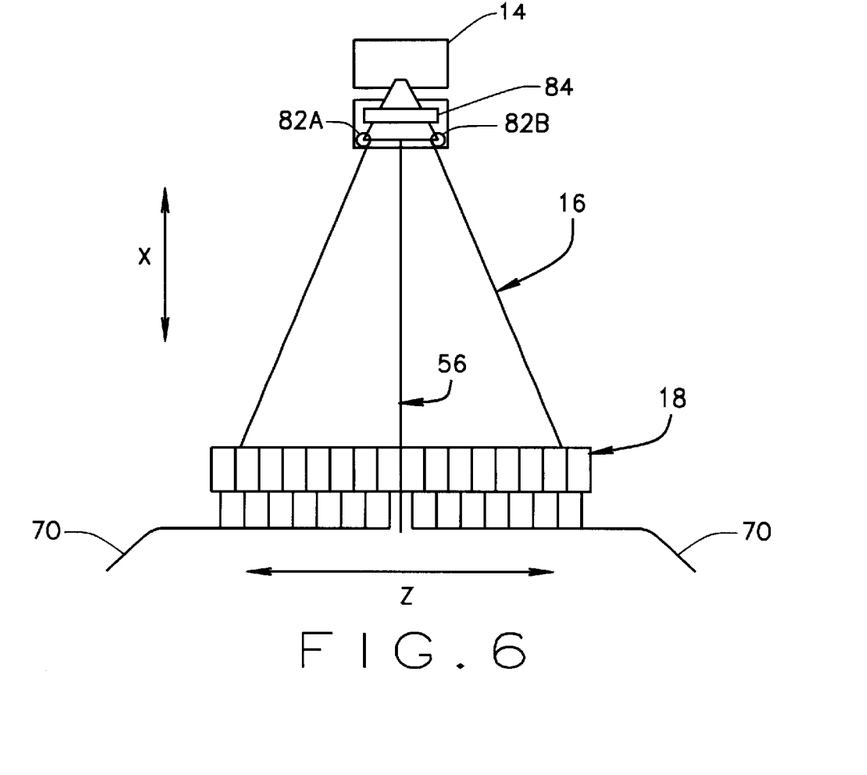
FIG. 6 is a schematic illustration of x-ray generation and detector components viewed from a side of the gantry.

In one embodiment and as shown in FIG. 6, illustrating a schematic illustration of system 10 viewed from a side of gantry 12, collimator 52 includes eccentric cams 82A and 82B, and a filtration device 84. The position of cams 82A and 82B is controlled by a collimator controller (not shown) which receives its commands from x-ray controller 28. Specifically, the collimator controller includes a cam drive or at least one cam motor 104, for altering the position of cams 82A and 82B. In addition, in one embodiment, the collimator controller includes a processing unit, or logic circuitry for controlling the cam drive and exchanging information with x-ray controller 28. In an alternative embodiment, the cam drive may be controlled directly by x-ray controller 28.

Cams 82A and 82B are positioned on opposing sides of fan beam axis 56 and may be independently adjusted with respect to the spacing between cams 82A and 82B and their location relative to fan beam axis 56. Cams 82A and 82B may be positioned with a single cam drive, or alternatively, each cam may be positioned with a separate cam drive. In other embodiments, collimator 52 may include additional cams and each cam may be coupled to a separate cam drive, for example cam motor or actuator, for altering the position of the cam. Cams 82A and 82B are fabricated from an x-ray absorbing material, for example, tungsten and are coupled to the cam motors utilizing accurate ball bearings (not shown).

For example and in one embodiment, separate stepper motors (not shown) are connected to respective cams 82A and 82B for precisely controlling the position of cams 82A and 82B so that each cam may be independently positioned. As a result of the eccentric shape, the rotation of respective cams 82A and 82B alters the slice thickness of x-ray beam 16. In addition, the independent adjustment of cams 82A and 82B allows for z-axis correction of focal spot motion of x-ray source 14, minimizes slice thickness variation from x-ray source to x-ray source variations, and allows faster CT scanner rotation. Specifically, eccentric cams 82A and 82B reduces frictional changes due to centripetal loading because the additional forces caused by gantry rotation are normal to the bearing load carrying capability. As a result, cams 82A and 82B allow highly accurate and repeatable aperture positioning, even under extreme gantry rotations.

Figure 7:
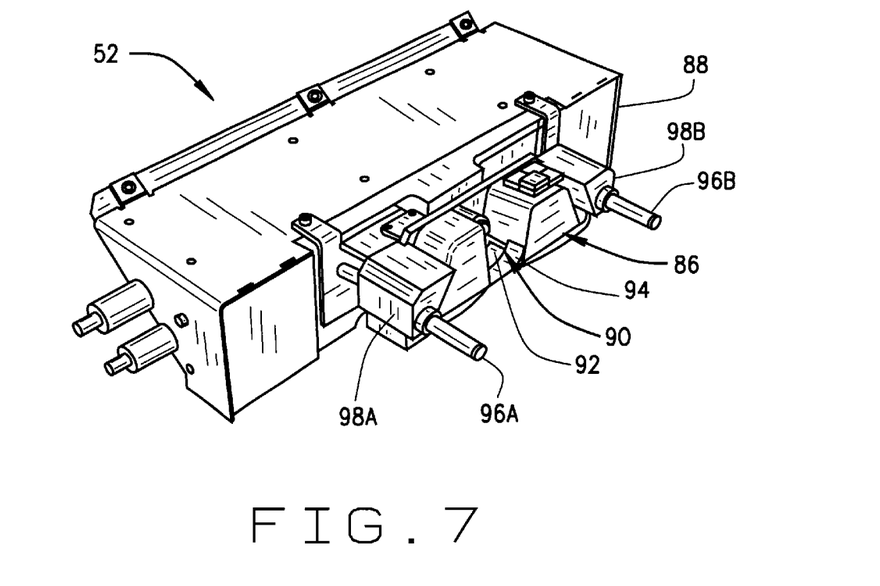
FIG. 7 is a perspective illustration of the collimator illustrated in FIG. 3.
Figure 10:
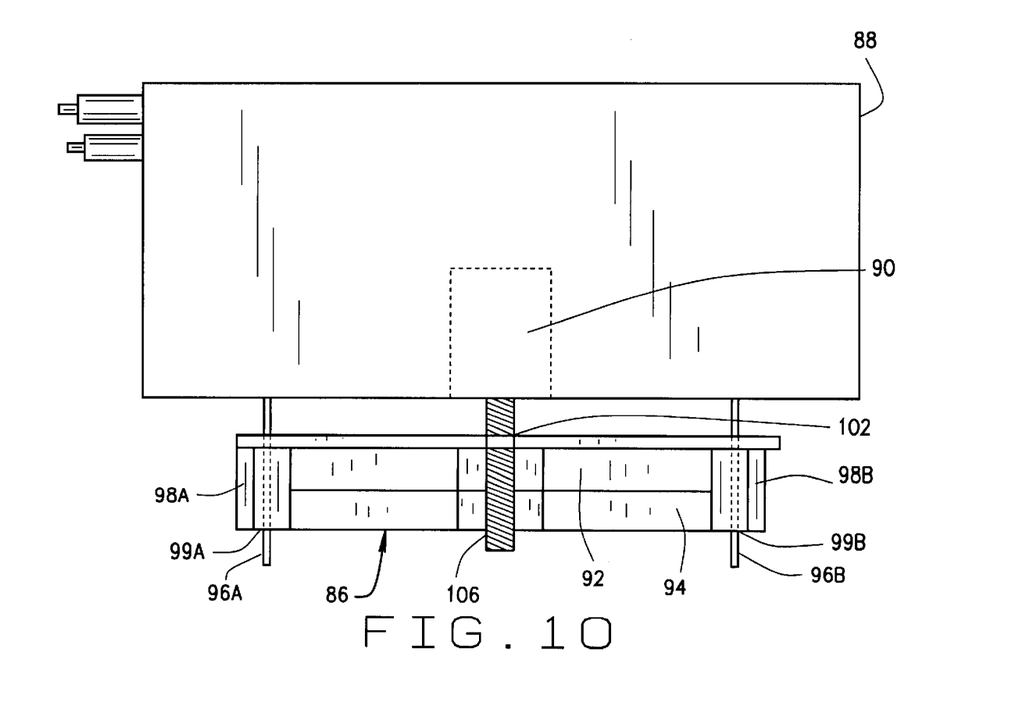
FIG. 10 is a perspective view of the collimator and filter device in FIG. 7.

As shown in FIG. 7 and FIG. 10, pre-patient collimator 52 further includes a movable filtration device 86, a housing 88, and a filter drive, or filter motor 90 for altering the position of filtration device 86 relative to housing 88. Specifically, and in one embodiment, filtration device 86 includes a first filter 92 and a second filter 94. Filters 92 and 94 are positioned so that x-ray beam 16 projects through respective filters 92 and 94. By altering the position of filters 92 and 94 relative to housing 88 utilizing filter motor 90, the dosage of x-rays from source 14 to patient 22 is altered. For example, filtration device 86 may be a bowtie filter and may include any number of filters. In other embodiments, filter drive 90 may be a stepper motor, actuator, or other displacement type device. Pre-patient collimator 52 further includes two shafts 96A and 96B extending from housing 88 so that shafts 96A and 96B are perpendicular to the x-ray fan beam axis 56.

Filtration device 86 further includes linear bearings 98A and 98B coupled to shaft openings 99A and 99B and shafts 96A and 96B. Linear bearings 98A and 98B are configured to slidably engage respective shafts 96A and 96B and allow filtration device 86 to move filters 92 and 94 perpendicular relative to x-ray beam axis 56. Utilizing filter motor 90, filtration device 86 may be moved, or positioned, toward or away from housing 88. Specifically, and in one embodiment, filter motor 90 is a lead-screw motor and filtration device 86 includes a threaded lead-screw 102 configured to threadedly receive a lead-screw shaft 106 of lead-screw motor 90. By energizing the lead-screw motor in one direction, filtration device 86 is moved toward housing 88. Reversing the direction of the lead-screw motor moves filtration device 86 away from housing 88.

Altering the position of filtration housing 86 modifies, or alters, the dosage of x-ray beam received by patient 22 by changing location of filtration device 86, specifically, the position of filters 92 and 94. For example, filters 92 and 94 may be combined in one of four combinations to alter x-ray beam 16. Specifically and in one embodiment, filters 92 and 94 may be positioned in a calibration mode, a body region mode, a head mode, or a block mode. These modes are defined by the amount of x-ray beam 16 that is allowed to pass through filters 92 and 94 as a function of location.

Figure 8:
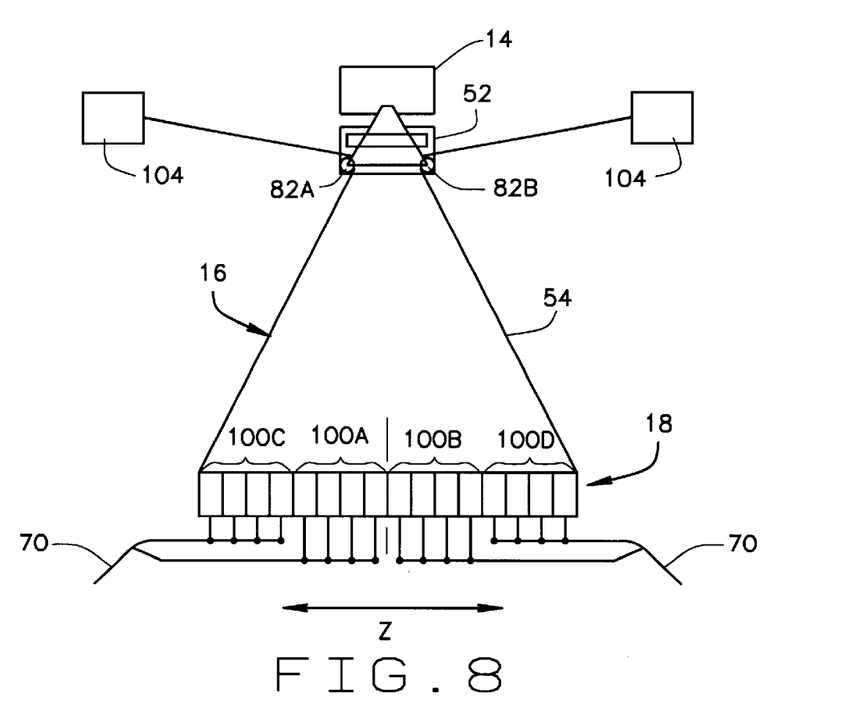
FIGS. 8 schematically illustrates collection of scan data for a four slice and 5.0 mm slice thickness configuration.

In operation, the operator determines an appropriate thickness and quantity of slices as required by the scan procedure to be performed. Detector array 18 and collimator 52 are then configured for the desired slice thickness and quantity. The configuration of detector array 18 and collimator 52 minimize the x-ray dosage to patient 22 and improve stability and efficiency of x-ray beam 16 by fully utilizing the z-axis of x-ray beam 16. Specifically, as shown in FIG. 8, detector 18 is divided into a number of slices 100. The thickness of each slice 100 is determined by the number of photodiode array outputs that are combined using switch apparatus 66 and by adjusting the position of collimator cams 82 and 84B in the z-axis direction and respective filters 92 and 94, as defined by the operator.

For example, if the operator selects four slices of 5.0 mm, system 10 may be configured as shown in FIG. 8. Particularly, the outputs of the photodiode array are combined, using switch apparatus 66, to form slices 100A, 100B, 100C and 100D, each having a slice thickness of 5.0 mm where each row of detector module 20 is 1.25 mm wide.

Specifically, four outputs of the photodiode array are electrically coupled by switch apparatus 66 to form slice 100A. Respective slices 100B, 100C and 100D are each similarly formed by combining four outputs of the photodiode array. Collimator cams 82A and 82B are separated in the z-axis direction to provide 20.0 mm of source collimation. Slice data from slices 100A, 100B, 100C and 100D are supplied to DAS 32 via cable 70.

Figure 9:
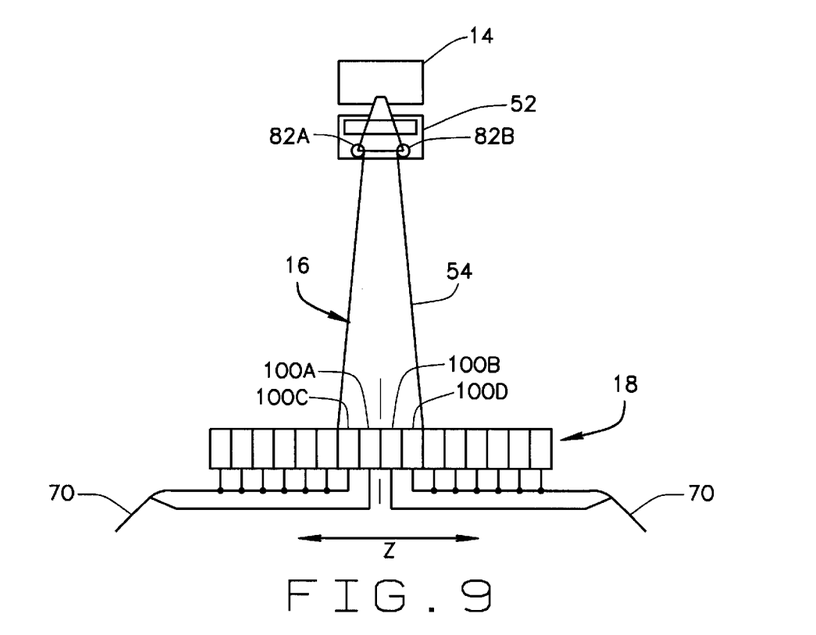
FIGS. 9 schematically illustrates collection of scan data for a four slice and 1.25 mm slice thickness configuration.

For four slices of data with a 1.25 mm slice thickness, the detector configuration shown in FIG. 9 may be utilized. Particularly, the photodiode array outputs form four slices 100A, 100B, 100C and 100D, each having a thickness of 1.25 mm. Cams 82A and 82B are not separated as wide apart as for the 20 mm slice thickness (FIG. 8). Rather, cams 82A and 82B are moved closer together in the z-axis direction to provide 5.0 mm collimation. In one embodiment, although slices 100C and 100D are defined by collimator 52 to have a thickness of 1.25 mm each, the remaining outputs of photodiode array 52 are combined for slices 100C and 100D using switch apparatus 66. Particularly, seven outputs of the photodiode array are combined by switch apparatus 66 to gather data for slice 100C. Similarly, seven outputs of the photodiode array are combined to gather data for slice 100D. Referring now to slices 100A and 100B, data is gathered from one output of the photodiode array for slice 100A and from one output of the photodiode array for slice 100B. Data from slices 100A, 100B, 100C and 100D are supplied to DAS 32 via flex cables 70. Of course, many other combinations of slice thickness and quantity are possible using system 10.

In addition to altering the slice thickness of x-ray beam 16, cams 82A and 82B may be utilized to correct for z-axis motion and tube to tube variation of x-ray source 14. Specifically, utilizing known methods for determining focal spot position, the position of cams 82A and 82B may be independently altered to compensate, or adjust, for z-axis motion of the x-ray beam 16. More specifically, and in one embodiment, based upon the focal spot position, respective cams 82A and 82B are independently positioned utilizing the cam motor so that the focal spot of x-ray beam 16 is properly positioned. Cams 82A and 82B may also be utilized to compensate for non-uniformity of the z-axis motion of x-ray beam 16 by altering the position of one respective cams 82A and 82B. For example, as x-ray source 16 heats up, x-ray beam axis 56 may become no longer centered on detector 18. The non-centered x-ray beam may be repositioned to the center by altering at least one of cams 82A and 82B utilizing the cam motors.

Additionally, based on the mode of operation for system 10, the position of filtration device 86 is adjusted so that the x-ray dosage is appropriate for the test to be performed. Specifically, based on the mode selected by the operator, the position of filtration device 86 is altered so that patient 22 is exposed to the proper x-ray beam 16. More specifically, the position of filtration device 86 is altered by energizing filter motor 90 so that filtration device 86 is retracted toward or extended away from housing 88 so that x-ray beam 16 passes through appropriate filters 92 and 94. For example, if the head of patient 22 is to be scanned, motor 90 may position filtration device at a known location so that filter 94 reduces x-ray beam 16 to a head mode type of exposure. In performing a CT scan of a head of patient 22, motor 90 positions filtration device 86 so that filters 92 and 94 are properly positioned relative to housing 88. More particularly, motor 90 is energized so that filtration device 86 is, for example, retracted toward housing 88 so that filters 92 and 94 are properly positioned.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

The above described CT system enables selection of the number and thickness of slices to reduce patient x-ray dosage improve x-ray beam efficiency. In addition, the pre-patient collimator enables z-axis correction, reduces slice thickness variations and selectable filtering of the x-ray beam.

What is claimed is:

1. A pre-patient collimator for altering the x-ray exposure in a computed tomography system, the computed tomography system comprising an x-ray source and a detector array, said collimator comprising:

a plurality of eccentric cams, at least a first cam and a second cam positioned on opposing sides of a fan beam radiated from the x-ray source, the fan beam having a thickness in a z-axis direction; and at least one cam drive configured to position said cams to adjust the fan beam;

said collimator further configured to independently alter positions of said eccentric cams to compensate for z-axis motion of the x-ray fan beam in response to a determined focal spot position of the x-ray fan beam.

2. A collimator in accordance with claim 1 further configured to compensate for non-uniformity of z-axis motion of the fan beam radiated from the x-ray source as the x-ray source heats up.

3. A collimator in accordance with claim 2 wherein said detector array comprises a multislice detector and wherein said cam drive further configured to alter a fan beam slice thickness.

4. A collimator in accordance with claim 1 wherein to compensate for z-axis motion of the x-ray fan beam, said collimator is configured to rotate said eccentric cams.

5. A collimator in accordance with claim 4 wherein said cam drive comprises at least one cam motor.

6. A collimator in accordance with claim 5 wherein said cam drive comprises a cam motor for each cam.

7. A collimator in accordance with claim 6 wherein said first cam coupled to said first cam motor and said second cam coupled to said second cam motor.

8. A collimator in accordance with claim 4 further comprising:

a filtration device comprising a plurality of filters;

a housing; and a filter drive for altering position of said filtration device, said filter drive coupled to said housing and said filtration device.

9. A collimator in accordance with claim 8 further configured to compensate for non-uniformity of z-axis motion of the fan beam radiated from the x-ray source as the x-ray source heats up.

10. A collimator in accordance with claim 9 wherein the x-ray fan beam projects from an x-ray beam axis and wherein said filter drive comprising a plurality of shafts extending perpendicular to the x-ray fan beam axis from said housing.

11. A collimator in accordance with claim 10 wherein said filtration device further comprises plurality of shaft openings configured to receive said shafts.

12. A collimator in accordance with claim 11 wherein said filter drive comprising a motor coupled to said housing and configured to extend and retract said filtration device perpendicular to the fan beam axis from said housing.

13. A collimator in accordance with claim 12 wherein said motor comprises a lead-screw motor having a threaded shaft and wherein said filtration device further comprises a lead-screw opening configured to threadedly engaged said lead screw shaft.

14. A collimator in accordance with claim 11 wherein said filtration device further comprising a linear bearing coupled to each shaft opening and configured to slidably engage said shaft.

15. A collimator in accordance with claim 1 further configured so that rotation of said eccentric cams adjusts a thickness of the fan beam.

16. A system for reducing x-ray exposure in a computed tomography system, the computed tomography system including an x-ray source emitting an x-ray fan beam, a pre-patient collimator comprising a plurality of eccentric cams and a plurality of filters and a detector array comprising a plurality of detector cells extending in a z-axis, said system configured to:

combine a number of detector cells to form at least one slice;

position the pre-patient collimator to define an x-ray thickness, location and exposure by rotating the eccentric cams of said collimator; and independently alter positions of said eccentric cams to compensate for z-axis motion of the x-ray fan beam in response to a determined focal spot position of the x-ray fan beam.

17. A system in accordance with claim 16 further configured to compensate for non-uniformity of z-axis motion of the fan beam radiated from the x-ray source as the x-ray source heats up.

18. A system in accordance with claim 16 further configured so that rotation of said eccentric cams adjusts a thickness of the fan beam.

19. A pre-patient collimator for altering the x-ray exposure in a computed tomography system, the computed tomography system comprising an x-ray source and a detector array, said collimator comprising:

a plurality of eccentric cams fabricated from an x-ray absorbing material, at least a first cam and a second cam positioned on opposing sides of a fan beam radiated from the x-ray source, said cams configured to block a portion of the x-ray fan beam;

a cam drive for adjusting the fan beam, said cam drive coupled to said cams;

a filtration device;

a housing; and a filter drive for altering position of said filtration device, said filter drive coupled to said housing and said filtration device;

said collimator configured to independently alter positions of said eccentric cams to compensate for z-axis motion of the x-ray fan beam in response to a determined focal spot position of the x-ray fan beam.

20. A collimator in accordance with claim 19 wherein said cam drive comprises a cam motor for each cam.

21. A collimator in accordance with claim 20 wherein said first cam coupled to said first cam motor and said second cam coupled to said second cam motor.

22. A collimator in accordance with claim 19 wherein said detector array comprises a multislice detector and wherein said cam drive configured to alter a fan beam slice thickness.

23. A collimator in accordance with claim 19 further configured to compensate for non-uniformity of z-axis of the fan beam radiated from the x-ray source as the x-ray source heats up.

24. A collimator in accordance with claim 19 further configured so that rotation of said eccentric cams adjusts a thickness of the fan beam.

* * * * *

UNITED STATES PATENT AND TRADEMARK OFFICE
CERTIFICATE OF CORRECTION

PATENT NO.    : 6,298,117 B1
DATED         : October 2, 2001
INVENTOR(S)   : Willi W. Hampel et al.

It is certified that error appears in the above-identified patent and that said Letters Patent is hereby corrected as shown below:

Column 3,
Line 8, delete "FIGS." and insert therefor -- FIG. --.
Line 10, delete "FIGS." and insert therefor -- FIG. --.

Column 4,
Line 67, delete "disable" and insert therefor -- disabled --.

Column 9,
Line 8, delete "engaged" and insert therefor -- engage --.

Signed and Sealed this

Thirteenth Day of May, 2003

JAMES E. ROGAN
*Director of the United States Patent and Trademark Office*